US00PP37340P3

(12) United States Plant Patent
Hall

(10) Patent No.: US PP37,340 P3
(45) Date of Patent: Mar. 24, 2026

(54) BLACK RASPBERRY PLANT NAMED 'Shekinah Tahi'

(50) Latin Name: *Rubus occidentalis*
Varietal Denomination: Shekinah Tahi

(71) Applicant: Harvey Hall, Rotorua (NZ)

(72) Inventor: Harvey Hall, Rotorua (NZ)

( * ) Notice: Subject to any disclaimer, the term of this patent is extended or adjusted under 35 U.S.C. 154(b) by 0 days.

(21) Appl. No.: 18/890,521

(22) Filed: Sep. 19, 2024

(65) Prior Publication Data

US 2025/0107474 P1 Mar. 27, 2025

Related U.S. Application Data

(60) Provisional application No. 63/585,412, filed on Sep. 26, 2023.

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./203, 204
See application file for complete search history.

(56) References Cited

PUBLICATIONS https://pluto.upov.int/result; UPOV-PLUTO Plant Variety Databse; Retreived from the Internet on Mar. 3, 2025. Citation for 'Shekinah Tahi' (Year: 2022).*

* cited by examiner

*Primary Examiner* — Zachariah Allan Kay
(74) *Attorney, Agent, or Firm* — Panitch Schwarze Belisario & Nadel LLP; Stephany G. Small; Travis W. Bliss

(57) ABSTRACT

A new and distinct cultivar of spineless, floricane fruiting black raspberry 'Shekinah Tahi'. Canes of 'Shekinah Tahi' have no spines, unlike the usual spiny canes of black raspberries. The spineless trait was introgressed from the original red raspberry source that originated in the old Scottish variety 'Burnetholm'. The new cultivar fruits on laterals grown from buds of overwintered floricanes. 'Shekinah Tahi' produces large fruits in tight bunches on the ends of long spineless laterals.

7 Drawing Sheets

Latin name of genus and species: *Rubus occidentalis*.
Variety denomination: 'Shekinah Tahi'.

BACKGROUND OF THE INVENTION

The present invention relates to a new and distinct cultivar of spineless black raspberry, *Rubus occidentalis*. The new cultivar is distinguished from other black raspberry cultivars by being completely spineless in every part of the plant. Fruit is produced on floricanes giving mid-season production. 'Shekinah Tahi' fruit are too hard to pick for machine harvest, process production. 'Shekinah Tahi' fruit are too tightly bunched and not firm enough for fresh market commercial sales. 'Shekinah Tahi' offers significant opportunities for home gardeners as an easy to manage spineless variety. Traditional spiny black raspberries require considerable input for management and in the home garden 'Shekinah Tahi' will provide a welcome alternative.

DESCRIPTION OF RELATED PRIOR ART

Black raspberries are well known for forming few or no suckers from their roots and new canes come from the basal crown of the plant. Traditional black raspberries are very spiny and they display a rambling growth because canes are arching and spreading, unlike the more upright growth of red raspberries. The spreading growth of black raspberries makes them difficult to manage, especially in a home garden situation. Traditional management practices to contain the plants involve cane tipping to reduce height, making the plants bushy, branching and low growing. When cane tips of the arching canes of black raspberries touch the ground, they form roots, especially in the Fall. A new plant is formed at each point where a cane tip produces roots, making them difficult to confine to one spot within a garden. A management practice of tipping black raspberries at about 1 m tall (around 3 feet) has been developed to limit tip-rooting and to promote significant branching and increased production of the new primocanes.

Hybrids between the black raspberry, *Rubus occidentalis* and the red raspberry, *Rubus idaeus*, are well known and are known as purple raspberries for their fruit color. Purple raspberries (*Rubus neglectus* L.) frequently do not tip root or produce suckers. In breeding of new black or red raspberry varieties, it is desirable to access traits from the other species. However, in practice it is difficult to breed traits from one species into the other and it takes multiple generations of breeding.

In red raspberries, the trait of fruit firmness was introgressed from the old black raspberry cultivar 'Cumberland'. Dark color was the major obstacle to overcome to get back to acceptable red raspberry color.

When attempting to move traits from red raspberry into black raspberry there have also been challenges to get back to a true black color. When moving traits from red raspberry into black raspberries retention of purple fruit color is the obstacle. Incorporating the primocane fruiting trait into black raspberries took three generations, ending with back-crossing to black raspberry to produce 'Ohio's Treasure' (U.S. Plant Pat. No. 27,871 P3). This process was alleviated by the dominant inheritance of the primocane fruiting trait.

The introduction of the gene for spinelessness from red raspberry into black raspberry was made significantly more difficult because its inheritance is recessive. For expression of this trait, it is necessary to incorporate two copies of the spineless gene into the diploid plant. To get a spineless black raspberry spineless selections were crossed with black raspberry. Selections from these hybrids were then inbred to expose the trait by back-crossing, selfing, or sib crossing to see the expression of the trait. 'Shekinah Tahi' results from around an eight-generation sequence of crosses, selfing and back crossing to black raspberry. The process began with crosses between 'Munger' black raspberry and the spineless red raspberry selections 'SCRI 689/81' and 'SCRI 6921/21' in 1969 and 1970. 'SCRI 689/81' and 'SCRI 6921/21' themselves were 4 and 5 generations of breeding from the old red raspberry cultivar 'Burnetholm', the source of the genetically spineless trait. Hence 'Shekinah Tahi' is 12-13 generations away from 'Burnetholm'. 'Shekinah Tahi' was selected in 2010, over a period of 40 years since the original black raspberry cross in Scotland and as much as 65 years since the selection of 'AR1', a spineless selection derived from selfing 'Burnetholm'. 'Burnetholm' was reported to carry genetic spinelessness by D. Lewis in 1939 and the trait was linked with eglandular cotyledons, where glandular hairs were absent on the cotyledonary leaves of spineless plants (FIG. 7). 'AR1', the spiny selections '3A/69' and '3B/45' and their spineless derivatives 'S25/8', 'S29/97' and 'S29/122' were produced in the 1950s. A range of spineless red raspberry cultivars has been developed in Scotland, England and around the world.

Named varieties of black raspberry have been cultivated since the 1800's, firstly with selections collected from the wild and then later from open pollinated seedlings and deliberate crosses. Almost 200 clones were mentioned in Hedrick's "The Small Fruits of New York" in 1925, with the majority of them being collected from the wild or from chance seedlings. Around twenty varieties resulted from deliberately grown seedling populations, and only six were the result of a deliberate crosses, the majority being from open pollinated seed lots. From all the selections mentioned in Hedrick's book in 1925, only three have been retained to the present day, 'Cumberland', 'Munger' and 'Plum Farmer', all from the 1890s, with 'Munger' being still the cultivar of choice for machine harvest, process production in Oregon. The genetic diversity of black raspberry *Rubus occidentalis* L. described in 1925 included black, yellow, orange and white fruited types, with or without bloom on the fruits and canes, and it also included two spineless varieties, Davison (1859) and Fay (1874). No record exists of these two varieties being used for breeding and it is assumed that the varieties have been lost.

Until the advent of more recent collections and their study the black raspberry was believed to have limited genetic diversity. However, limited genetic diversity was shown to be solely amongst the present range of cultivars and there was found considerable diversity amongst wild black raspberries. (Michael Dossett, Nahala Bassil, Kim Lewers and Chad Finn 2012: Genetic Diversity in wild and cultivated black raspberry (*Rubus occidentalis* L.) evaluated by simple sequence repeat markers—Genetic Resources and Crop Evolution 59. 10.1007/s10722-012-9808-8.). In the absence of the diversity as found in wild collections, and as represented in The Small Fruits of New York in 1925, the spineless trait and the floricane fruiting traits have been introgressed from red raspberry into the black raspberry through the work initiated by Derek Jennings in Scotland and carried out by Harry Swartz in Maryland respectively. In red raspberries the tendency in recent years has been to develop dual cropping varieties that bear a crop on the tips of the new primocanes and another crop on the floricanes in the following spring and summer. Economically this has become important as there are two production periods on the same variety and a spread of the marketing of the fruit. In black raspberry the production of cultivars bearing a primocane crop and a floricane crop has also been a desirable breeding objective and the primocane trait was sought from red raspberries, leading to the development and release of 'Ohio's Treasure' U.S. Plant Pat. No. 27,871 P3, a variety with small (1-2.6 g), rather soft fruit. The primocane fruiting habit also has been developed from purely black raspberry genetics, with crosses between selections of wild types, leading to the release of the two black raspberry cultivars 'Explorer' and 'Niwot'. 'Explorer' has since been discarded due to the lack of self-fertility and 'Niwot' is being recognised for its primocane and floricane production. 'Jewel' has large fruit for a variety solely derived from *Rubus occidentalis* L. black raspberry. The origin of 'Jewel' is reported to be 'Dundee x' (Bristol x Dundee) in the 1973 release notice. However, in "Genetic Diversity in wild and cultivated black raspberry (*Rubus occidentalis* L.) evaluated by simple sequence repeat markers" this origin is questioned, and the derivation is suggested to be from 'Huron' or 'Rachel', and 'Dundee'. Plants of 'Jewel' are vigorous, erect, winter hardy, consistently productive and canes are very spiny, typical of black raspberries. Fruiting is mid-season and fruit of 'Jewel' are firm, glossy and flavorful. 'Jewel' appears to be more disease resistant than most other black raspberries and it has slight susceptibility to powdery mildew and resistance to anthracnose. Fruit of 'Jewel' have a moderately tight cluster at the tip of fruiting laterals, and it exhibits concentrated ripening and a short production period. Sun scald of the plant and fruit may be a problem during hot weather conditions.

SUMMARY OF THE INVENTION

The present invention relates to a new and distinct cultivated variety (cultivar) of black raspberry, unique because of its genetically stable, completely spineless canes. The new cultivar is distinguished from other black raspberry cultivars by its completely spineless canes and black fruit. This is unlike the usual purple raspberries, from the hybrid origin, of a black-red raspberry cross. 'Shekinah Tahi' fruits on long, totally spineless, floricane laterals having tight clusters of fruit at lateral tips and some individual or paired fruits at the lateral leaf nodes, resulting in a moderately long season crop of large attractive black fruit. 'Shekinah Tahi' fruit have moderate firmness, making them unsuitable for shipping or for a long shelf life in the commercial market chain. However, they will last well for a home gardener or a U-Pick operation. Fruit release from the receptacle with moderate retention strength, making 'Shekinah Tahi' unsuitable for machine harvest-process production, with best quality fruit only being picked by hand harvest. 'Shekinah Tahi' produces a high yield of large fruit, and combined with the spineless canes makes the variety highly suited for the home garden producer. The spineless, vigorous, and semi-upright canes of 'Shekinah Tahi' also have a reduced ability to tip root, producing less spawn of new plants than either traditional spiny black raspberries, or from the suckers which are usual with red raspberries. 'Shekinah Tahi' pruning and training may be handled in a similar way to red raspberry, with no need to tip prune, making it possible for tall canes to be grown on a trellis and tipped when dormant during winter.

ORIGIN OF THE NEW CULTIVAR

The new cultivar of black raspberry arose from the original importation to New Zealand of open pollinated seed from Dundee, Scotland of a selection named 'SCRI 8232C9' which was from the cross of the two spiny selections 'SCRI 7861D13' x 'SCRI 7860D8'. 'SCRI 7861D13' was from the cross 'Munger' x 'SCRI 7562B10', a first backcross to black raspberry. The spineless selection 'SCRI 7562B10' came from the cross of 'SCRI 7251/31' ('Munger' x 'SCRI 6921/21') x 'SCRI 7346/3' ('Munger' x 'SCRI 689/81'). 'SCRI 7860D8' was from the cross 'Munger' x 'SCRI 7560C11', another first backcross to black raspberry. The spineless selection 'SCRI 7560C11' came from the cross of 'SCRI 7251/56' ('Munger' x 'SCRI 6921/21') x '7346/3' ('Munger' x 'SCRI 689/81'). In New Zealand two selections were chosen from the open pollinated seedlings produced from 'SCRI 8232C9', 'V23' and 'V32'. Each of these selections was crossed with 'Jewel' black raspberry to produce a further generation of breeding improvement, the populations '88407' and '88407R' from intercrossing 'Jewel' and 'V23' and the populations '88408' and '88408R' from intercrossing 'Jewel' and 'V32' yielding 4 and 7 selections respectively, one of which was released as the variety 'Ebony' in New Zealand, with purple fruit. In the following generation 8 selections were intercrossed, giving a further 11 selections. In 1995 seedlings from crosses between red raspberries were grown on the Hall family farm at Woodstock, New Zealand, and amongst them was a spineless black raspberry with black fruit of unknown origin which was designated 'Woodstock Black'.

'Shekinah Tahi' is a species hybrid with mostly black raspberry, *Rubus occidentalis* L. background, but with added traits from red raspberry *Rubus idaeus* L. including genetic spinelessness, the recessive gene s designating spine-free growth, improved uprightness and increased fruit size. The process by which these traits have been moved into the black raspberry is known as introgression which was begun by crossing the black raspberry seed parent 'Munger' with the spineless red raspberry pollen parents 'SCRI 6921/21' and 'SCRI 689/81'. In the first generation of seedlings all plants were spiny due to the dominant effect of the spiny genes from the black raspberry 'Munger'. In the second generation of breeding crosses between selections from the first generation gave seedlings which segregated for expression of spinelessness (ss) and spininess (genotypes Ss and SS) as designated by D Lewis in 1939 in his paper "Genetical studies in cultivated raspberries, I: inheritance and linkage" published in Journal of Genetics Vol. 38 Pages 367-379. Dominant spininess was represented by a capital S and the recessive spineless trait was represented by the lower case s, which needed to be present in a homozygous condition (ss) for the character to be expressed. Thus, the process continued with backcrosses to the black raspberries 'Munger' (SS) and 'Jewel' (SS), giving spiny seedlings in the first generation, followed by an inbreeding generation to allow the spineless trait (ss) to be expressed.

Spineless blackberries have genetic spinelessness through an analogous gene derived from the diploid (2×) blackberry species, *Rubus ulmifolius* var *inermis* (lacking thorns or spines). In breeding from *Rubus ulmifolius* var *inermis* tetraploid (4×) blackberries were produced by crossing with a spiny tetraploid wild type, and this was inbred to produce a spineless variety known as 'Merton Thornless'. 'Merton Thornless' was crossed with USA tetraploid blackberries to produce the varieties 'Smoothstem' and 'Thornfree', and 'Thornfree' formed the basis for breeding all the spineless varieties from the Arkansas breeding program and other programs around the world. With tetraploids the inheritance of the homozygous gene s (ssss) in breeding has different segregation ratios from diploid (2×) black and red raspberries, making it even more difficult to select transgressive segregants bearing the trait advancements desired for breeding improvement.

In each generation of breeding a predominating effect was occurring known as "linkage drag", where, due to the small-tight chromosomes "crossing over" events were limited and genuine change was hard to achieve. However, these changes are needed to shift spinelessness into a plant bearing black raspberry fruit but expressing the spineless trait. In the case of transferring the primocane fruiting trait from red raspberry into the black raspberry 'Ohio's Treasure' the process was simplified by the dominant inheritance of that trait, and a primocane fruiting essentially black raspberry cultivar was achieved within three generations of breeding. However, in the development of 'Shekinah Tahi' what was sought was for the recessive gene conferring the spineless trait to be transferred from its position on a red raspberry chromosome into the analogous position in the black raspberry genome. This process was held back at each generation of crossing, inbreeding and backcrossing by a range of other traits being carried forward from the red raspberry background. The introgression process was further complicated due to the necessity of the crossing over event needing to happen in both chromosomes bearing the spiny and spineless gene loci, so that undesirable traits from red raspberry would be left behind.

In the case of 'Shekinah Tahi', the introgression of the spineless trait into black raspberry was held back (linkage drag) by the purple color of the fruit typical of black raspberry x red raspberry hybrids being carried from one generation to the next. The breakthrough in getting a spineless derivative with black fruit was achieved by the selection of the chance seedling that was designated 'Woodstock Black', having both spineless growth and the desirable black fruit color.

In the process of introgression of black fruit color back into black raspberries linkage drag worked in favour of the variety development process through carrying some desirable traits along with the purple fruit color which was eventually lost. These have included improved fruit size and an improved cane growth uprightness into the new hybrid black raspberries.

'Shekinah Tahi' is the result of open pollination of an unnamed breeding seedling (not patented). The unnamed breeding seedling (i.e., female parent) originated from a cross between 'Woodstock Black' (not patented) and 'Jewel' (not patented). Bulk seedlings derived from the cross of 'Woodstock Black' (not patented) and 'Jewel' (not patented), including the female parent, were grown in 2009. After open pollination with the unnamed breeding seedling, the selection 'RZ10022' was chosen in 2010 for its very large black fruit, spineless canes and semi-upright growth habit. This selection 'RZ10022' has been multiplied vegetatively in New Zealand and assessed for its production and qualities and has been designated 'Shekinah Tahi'.

ASEXUAL PROPAGATION OF THE NEW CULTIVAR

'Shekinah Tahi' has been asexually propagated by tissue culture in Auckland, New Zealand and grown on in a commercial nursery in Nelson, New Zealand for assessment trials from 2010. No aberrant plants have been observed through all this asexual propagation and all plants have displayed similar spineless canes, growth and fruiting capabilities. Plants established in tissue culture without difficulty and multiplication in culture has been easy to achieve.

BRIEF DESCRIPTION OF THE DRAWINGS

The accompanying color photographs show typical specimens of the new variety at various stages of development (approximately one to two-years old plants) as true as it is possible to make in color reproduction. The color in the photographs may differ slightly from the color value cited in the detailed botanical description, which accurately describes the colors of 'Shekinah Tahi'.

DETAILED BOTANICAL DESCRIPTION

Figure 1:
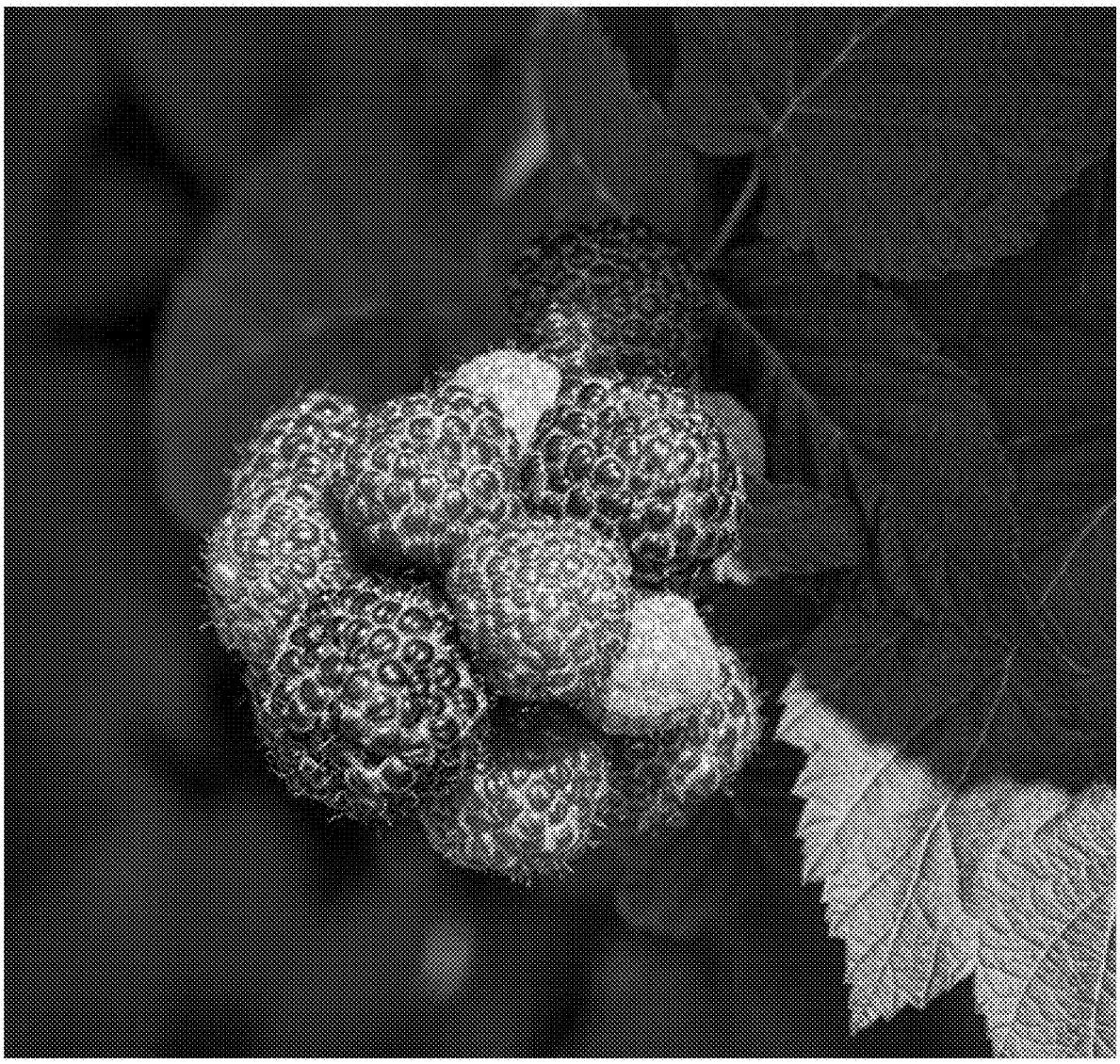
FIG. 1 shows a single fruiting lateral at the time of the ripening of the first fruit. Note the tightly clumped fruit at this stage of ripeness.
Figure 2:
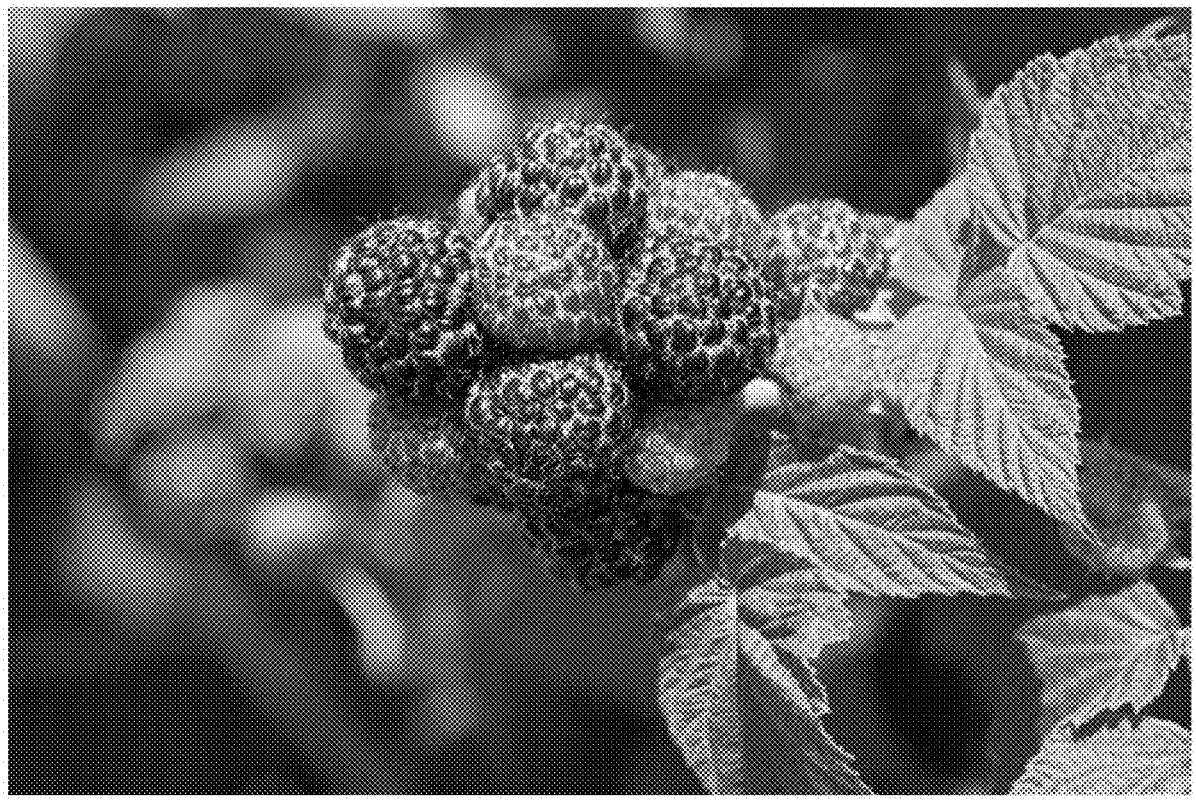
FIG. 2 shows a single fruiting lateral at a later stage of ripeness. Ripe fruit are still tightly clumped but are further separated than at the stage of first ripe fruit.
Figure 3:
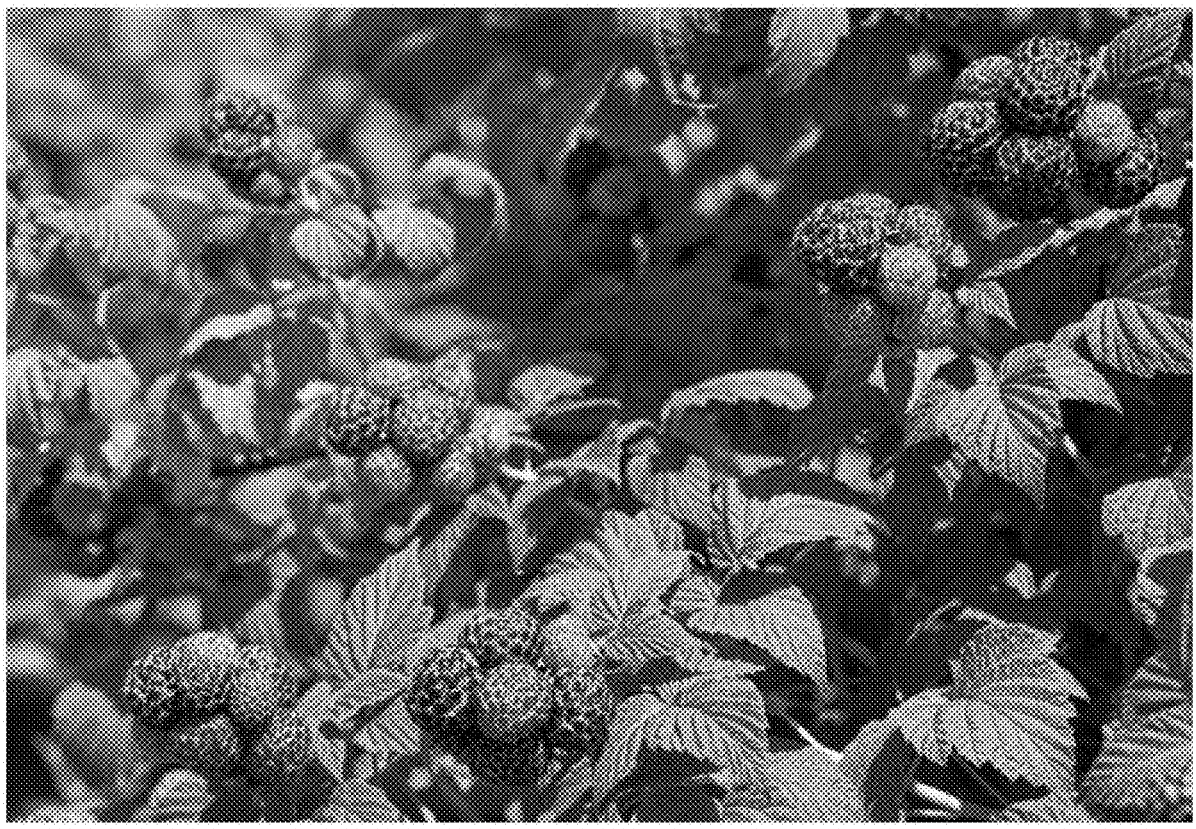
FIG. 3 shows several fruiting laterals with ripening fruit.
Figure 4:
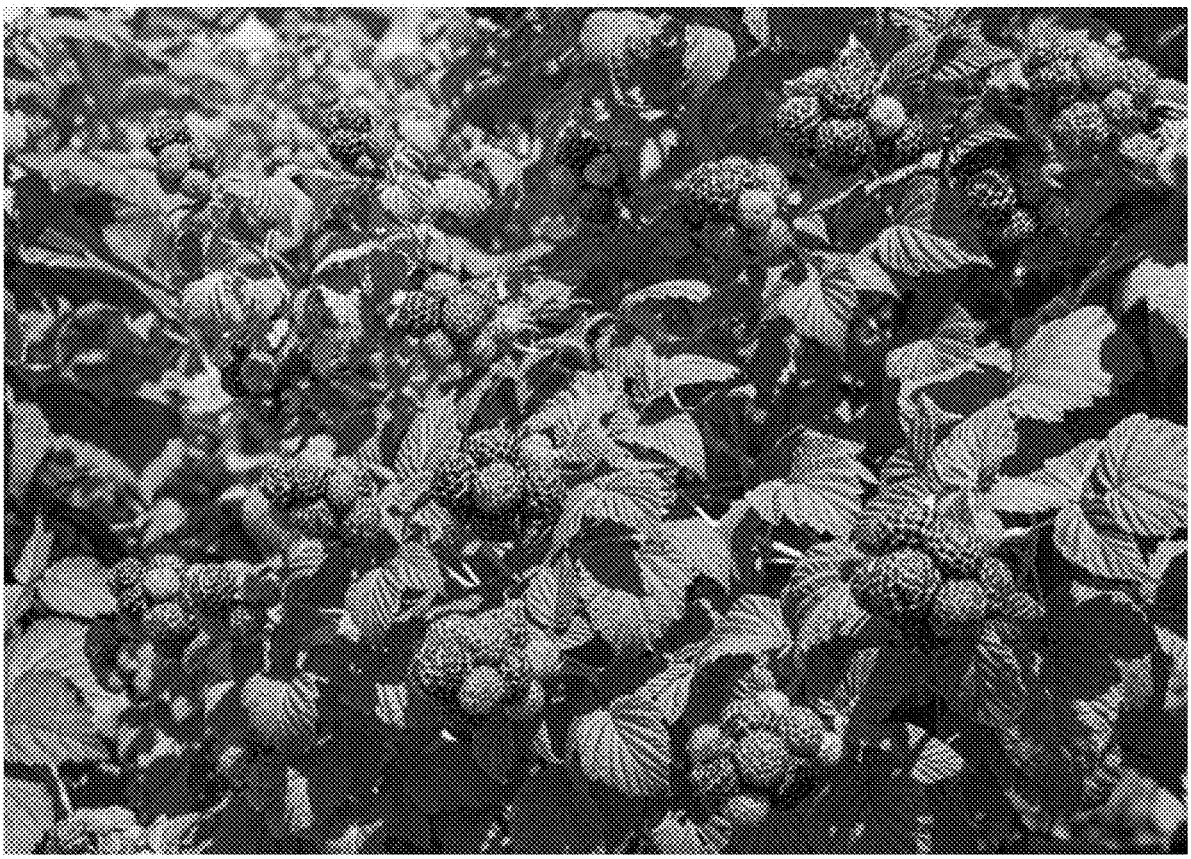
FIG. 4 shows a view of several canes and their fruit from further back.
Figure 5:
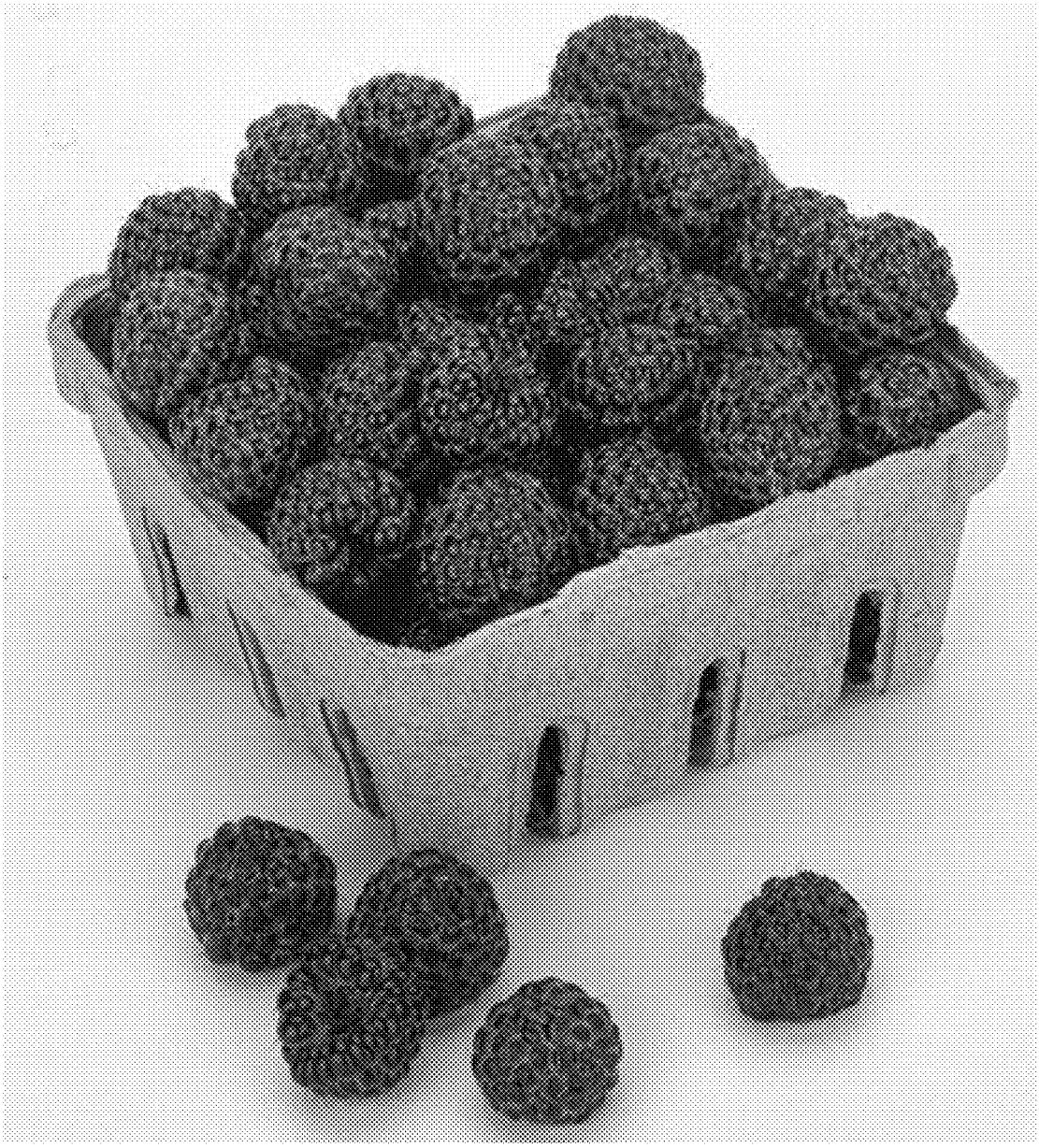
FIG. 5 shows a punnet of large and the high drupelet number and drupelet thickness of harvested fruit.
Figure 6:
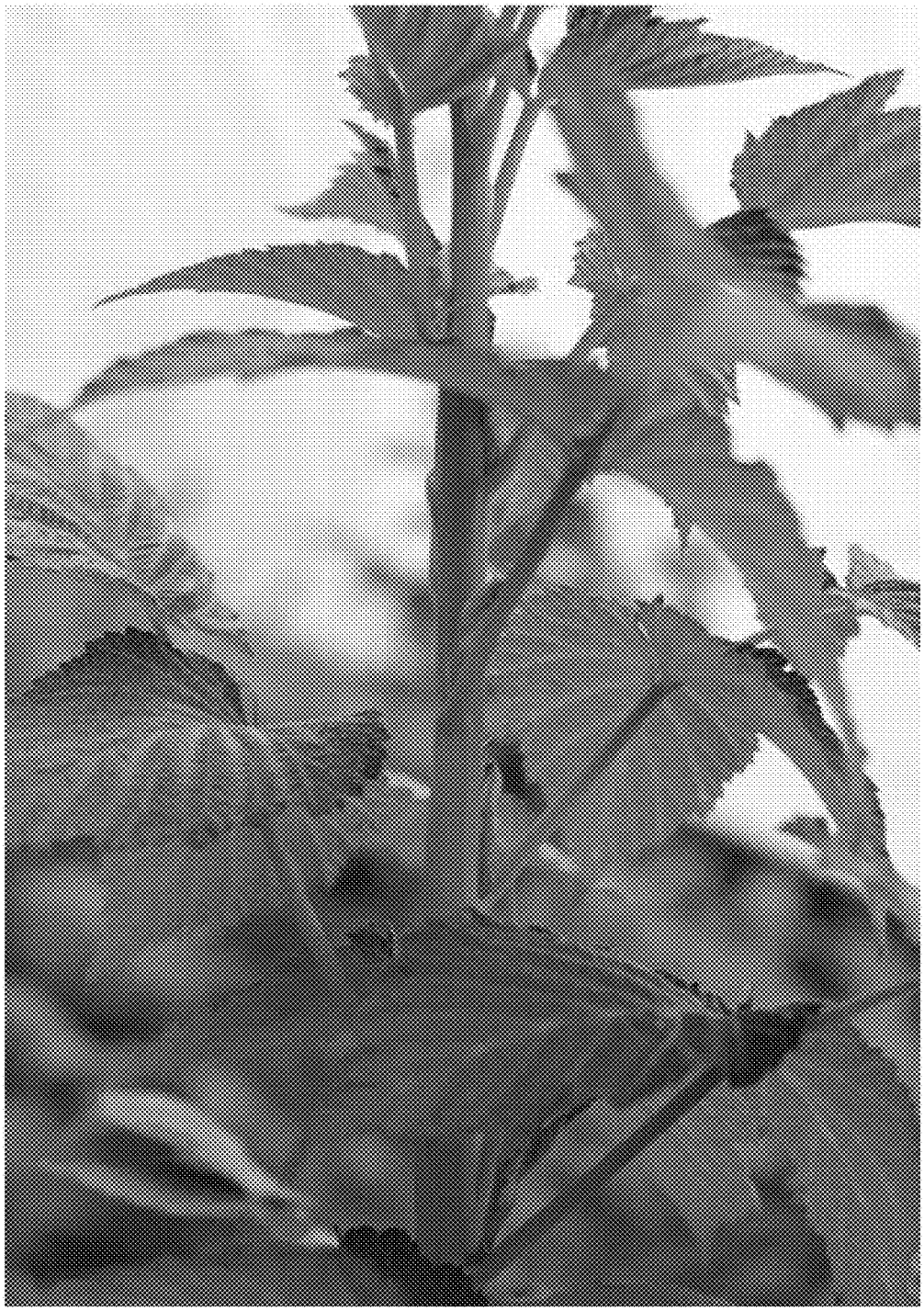
FIG. 6 shows a cane tip totally without spines and a view of the leafiness of new canes.
Figure 7:
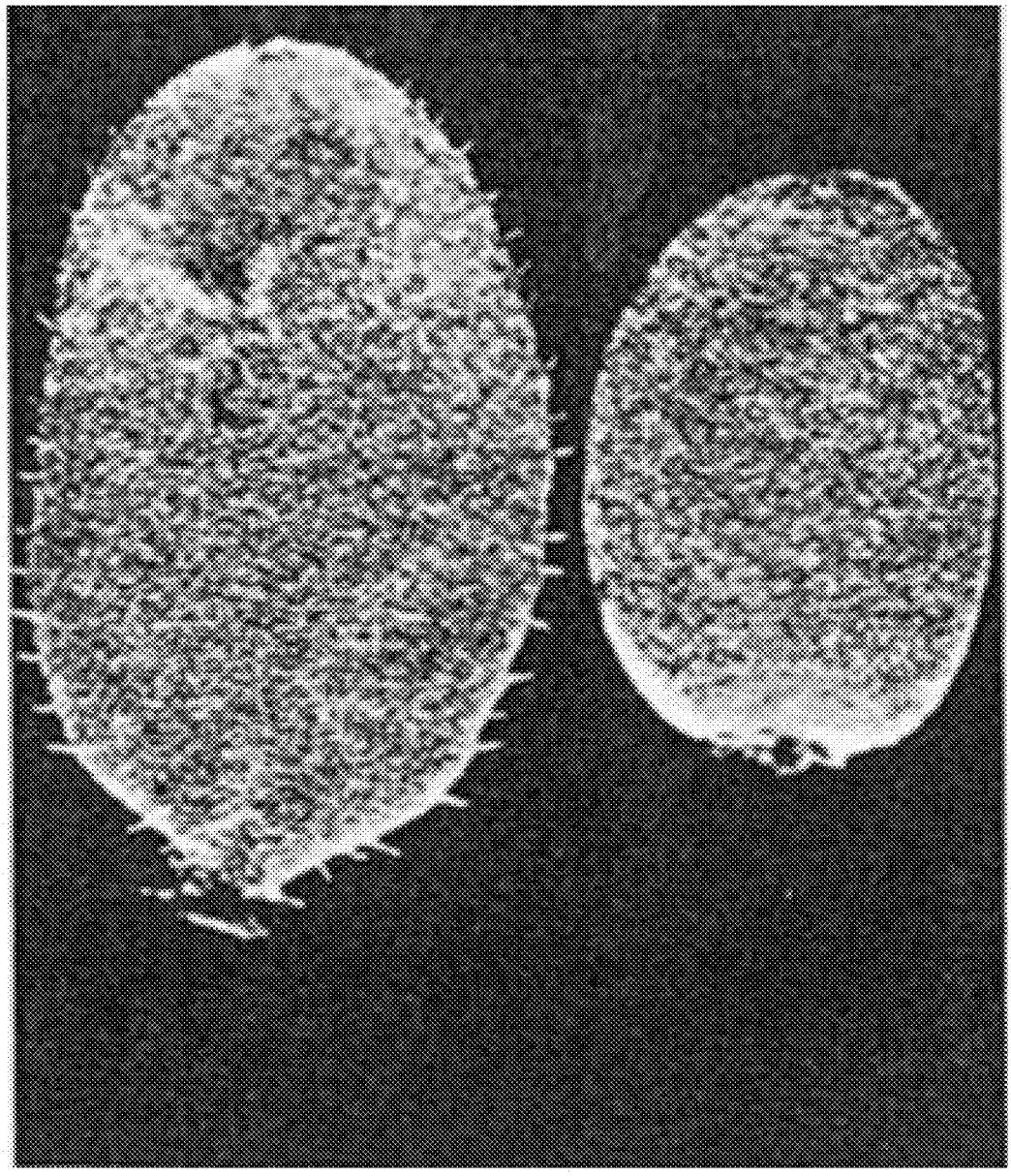
FIG. 7 shows cotyledonary leaves of spiny and spineless red raspberry as portrayed by D. Lewis in his 1939 paper: "Genetical studies in cultivated raspberries, I: inheritance and linkage" published in Journal of Genetics Vol. 38 Pages 367-379 as represented in Plate VIII, image 5.

The following is a description of the new variety using color terminology in accordance with The Royal Horticultural Society Color Charts (R.H.S.C.C.) 2015 edition.

The following is a detailed description of 'Shekinah Tahi' based on outdoor performance in Nelson province, New Zealand, and tunnel house performance in the Waikato and Bay of Plenty (other provinces in New Zealand). These observations have been extended and detailed by performance in Whately, Massachusetts where USA trials have been carried out. Observations and measurements have been made on plant morphology, fruit production and on post-harvest performance.

Propagation: 'Shekinah Tahi' propagates readily by tissue culture and plant growth is rejuvenated (rendered juvenile again) by this process. New plants from tissue culture in their first year tend to be more spreading than when they mature in year two and onwards. 'Shekinah Tahi' may sometimes propagate itself through tip rooting. Plants are grown on their own roots. Overall plant height 1.5-2 m depending on the growing location; plants are generally 2 m tall in New Zealand when grown outdoors in soil. Average plant width is dependent on being trained as planar plants on a trellis and when grown in this manner the width is 0.5-0.8 m. Roots extend 0.3-0.5 m from a crown.

Primocane: New cane growth of 'Shekinah Tahi' is almost exclusively from crown suckers but an occasional root sucker may be found. First year primocane growth is completely spineless and growth is entirely vegetative until after plants enter dormancy during fall and at the onset of winter. Primocanes of 'Shekinah Tahi' may be tipped as is usual with black raspberries for home garden or commercial cultivation, but may also be managed without cane tipping and pruned and trained like a red raspberry.

Spininess: Spines (prickles) are completely absent and self-pollinated seedlings all have eglandular cotyledons and grow completely spineless, similar to the spineless red raspberries produced in Scotland and around the world, and similar to the spineless blackberries from America and in other locations bearing spineless genes from *Rubus ulmifolius* var *inermis* (without spines or prickles).

Canes: Very young shoot: anthocyanin coloration of apex during rapid growth—present; floricane color in spring purpleish grey (N187C); spines—absent; generally 6-8 canes grow per crown, although this may be less or more under amended growing conditions; cane length—variable— according to the growing environment, age of the plant, the time of season planted and management. Primocanes of plants that have come through the previous winter in good condition will frequently exceed 2 m growth during the subsequent growing season. Cane color with bloom removed dark red (59A). Primocanes have strong, waxy coating that is easily removed by contact; cane cross section—generally circular; diameter at the base of canes—1-1.5 cm; primocane fruiting: absent.

Floricane growth and appearance: Begins with mid-season bud break and leads to flowering and fruiting in the same production season as 'Jewel'; dark purplish red (N79B); cane bloom is between very pale purple (91C) and light violet (91B).

Fruit: Berries are round in both latitudinal and longitudinal dimensions and are approximately 22-25 mm in diameter; general shape in lateral view-circular; color of fruit skin dark greyish purple (202A); fruit pulp dark greyish purple (202A); fruit juice of squashed fruit dark red (187A) less shiny appearance than 'Jewel' fruit; fruit are slightly softer than 'Jewel'; fruit main bearing type-only on previous year's cane in summer; time of fruit ripening on previous season's canes-very early to early (between 'Vene' and 'Glen Clova'); variety does not fruit on current season's cane in autumn; acidity: ~pH 3.6 Titratable acidity; Soluble Solids brix measurement ~12; timing of harvest—mid-season, similar to 'Jewel'; drupelet walls of 'Shekinah Tahi' fruit—thick; 'Shekinah Tahi' fruit are borne in very tight clusters, predominantly at the lateral tips.

Seed: Seed endocarp color light yellowish brown 199C.

Habit: Upright to semi-upright.

Emergence: Typically at the same time of 'Jewel' in the when planted together.

Leaves: Apex leaflet, length typically 3-5 cm, totally devoid of spines (i.e., prickles); leaf color upper side greyish olive green (NN137C); leaf color underside moderate yellow green (148B); leaf petiole moderate purplish red (59C); leaves grow alternately on the lateral, and are composed of 3 pinnately compound leaflets; the center leaflet is generally three-lobed; laterals leaf length variable from 20 to 75 cm from the top to base; palmate venation; arrangement of leaflets-overlapping; terminal leaflet: undulation—medium; leaf edges are serrated; surface texture of leaf is rugose.

Disease: No significant disease resistance or susceptibility observed compared with other black or red raspberries at Whately, Massachusetts.

Pests: No significant pest resistance or susceptibility observed compared with other black or red raspberries at Whately, Massachusetts.

Heat tolerance: 'Shekinah Tahi' has not displayed susceptibility to heat damage in conditions at Whately, Massachusetts.

Cold tolerance: 'Shekinah Tahi' has not displayed susceptibility to cold damage in conditions at Whately, Massachusetts. Plants appear to be hardy throughout USDA hardiness zones 3-8. The variety is hardy with little to no winter damage observed.

Flower: Unscented; flower cluster light yellowish green (140D); open flower greyish yellow green (194B).

Productivity: The plants of 'Shekinah Tahi' are productive, with almost the yield of 'Jewel'.

Inflorescence: Long floricane laterals with flowers bunched at the tips; timing of flowering similar time to 'Jewel'.

The following characteristics distinguish 'Shekinah Tahi' from other black raspberries:

When compared to similar known variety 'Munger', 'Shekinah Tahi' has a larger average fruit weight (4 grams compared to 2.5 grams) and is spine free, compared to 'Munger', which has spines present on the canes.

Fruit of 'Shekinah Tahi' have a higher drupelet number than 'Jewel'.

'Shekinah Tahi' canes have a stronger vigor than 'Jewel'.

Growth habit of 'Shekinah Tahi' appears to be more erect than 'Jewel'.

'Shekinah Tahi' leaves are larger than those of 'Jewel'.

The invention claimed is:

1. A new and distinct spineless black raspberry plant known as 'Shekinah Tahi' described herein, illustrated and identified by the characteristics presented herein.

* * * * *